United States Patent [19]
Sakurai et al.

[11] Patent Number: 5,925,792
[45] Date of Patent: Jul. 20, 1999

[54] PROCESS FOR PREPARING 2-AMINO-1,3-ALKANEDIOL OR DERIVATIVE THEREOF, PROCESS FOR PREPARING OPTICALLY ACTIVE DIHYDROSPHINGOSINE DERIVATIVE, AND INTERMEDIATES FOR OPTICALLY ACTIVE DIHYDROSPHINGOSINE DERIVATIVE

[75] Inventors: Kazutoshi Sakurai; Kenya Ishida, both of Kanagawa, Japan

[73] Assignee: Takasago International Corporation, Tokyo, Japan

[21] Appl. No.: 08/696,161

[22] Filed: Aug. 13, 1996

[30] Foreign Application Priority Data

Aug. 25, 1905 [JP] Japan .................................. 7-239045

[51] Int. Cl.$^6$ ................................................. C07C 209/00
[52] U.S. Cl. ............................................ 564/468; 562/553
[58] Field of Search .............................. 564/468; 562/553

[56] References Cited

U.S. PATENT DOCUMENTS

| | | |
|---|---|---|
| 4,691,037 | 9/1987 | Yoshikawa et al. ....................... 556/18 |
| 5,190,969 | 3/1993 | Blumenstein et al. ................... 549/548 |
| 5,530,150 | 6/1996 | Takaya et al. ............................. 556/18 |

FOREIGN PATENT DOCUMENTS

| | | | |
|---|---|---|---|
| 0 174 057 | 3/1986 | European Pat. Off. ......... | C07F 15/00 |
| 0 366 390 B1 | 5/1990 | European Pat. Off. ......... | C07F 15/00 |
| 0 519 763 A2 | 12/1992 | European Pat. Off. ....... | C07C 247/06 |
| 5-85924 | 4/1993 | Japan ............................... | A61K 7/48 |

OTHER PUBLICATIONS

Dongwei Cai et al., *J.Org.Chem.*, vol. 59, (1994), pp. 7180–7181, "Synthesis of Chiral 2,2'-Bis(diphenylphisphino)-1,1'-binaphthyl (BINAP) via a Novel Nickel-Catalyzed Phosphine Insertion".

Hidemasa Takaya et al., *J.Org.Chem.*, vol. 51, (1986), pp. 629–635, "Practical Synthesis of (R)–or (S)–2,2'-Bis(diarylphisphino)-1,1'-binaphthyls (BINAP)".

Nozomu Sakai et al., *J.Am.Chem.Soc.*, vol. 115, (1993), pp. 7033–7034, "Highly Enantioselective Hydroformylation of Olefins Catalyzed by New Phosphinephosphite–Rh(I) Complexes".

Braish et al., "Synthesis of (S,S)–and (R,R)–2–alkyl–2, 5–diazabicyclo[2.2.1]heptanes". J. Org. Chem., vol. 55, 1684–1687, 1990.

Abiko et al., "An improved, convenient procedure for reduction of amino acids to aminoalcohols: Use of NaBH4–H2SO4". Tetrahedron Letts., vol. 33(38), 5517–5518, 1992.

Corey et al., "an enantioselective synthesis of (2S, 3S)–and (2R, 3S)–3–hydroxyleucine". Tetrahedron Letts., vol. 33(45), 6735–6738, 1992.

Tetrahedron, vol. 50, No. 38, 1994, Matsuura et al, "Total Synthesis Of Micro–ginin, an Angiotensin–Converting Enzyme Inhibitory Pentapeptide from the Blue–Green Alga *Microcystis aeruginosa*".

Tetrahedron Letters, vol. 31, No. 45, 1990, Thijs et al, "A General Stereo–specific Synthesis of γ–Hydroxy–α,β–Unsaturated Esters".

Racueil Des Travaux Chimiques Des Pays–Bas, vol. 105, No. 9, 1986, "Synthesis of the Optical Antipodes of 4–alkyl–γ–lactones".

Tetrahedron, vol. 51, No. 41, 1995, van Aar et al, "Synthesis of (4R,5R)–Muricatacin and its (4R, 5S)–Analog by Sequential Use of the Photo–Induced Rearrangement of Epoxy Diazomethyl Ketones".

*Primary Examiner*—Jose' G. Dees
*Assistant Examiner*—Barbara Badio
*Attorney, Agent, or Firm*—Sughrue, Mion, Zinn, Macpeak & Seas, PLLC

[57] ABSTRACT

A process for preparing an optically active dihydrosphingosine derivative is disclosed, comprising reducing a (2R, 3R)-2-amino-3-hydroxyalkanoic acid derivative represented by formula (III):

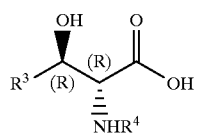

(III)

wherein $R^3$ represents a straight-chain alkyl group having 7 to 21 carbon atoms; and $R^4$ represents an amino group protecting group, (e.g., (2R,3R)-2-benzylamino-3-hydroxyoctadecanoic acid) with sodium tetrahydroborate in the presence of an acid. The process makes it feasible to produce an optically active dihydrosphingosine at high optical purity and through a simple process that is safe and easy to industrialize.

3 Claims, No Drawings

PROCESS FOR PREPARING 2-AMINO-1,3-ALKANEDIOL OR DERIVATIVE THEREOF, PROCESS FOR PREPARING OPTICALLY ACTIVE DIHYDROSPHINGOSINE DERIVATIVE, AND INTERMEDIATES FOR OPTICALLY ACTIVE DIHYDROSPHINGOSINE DERIVATIVE

FIELD OF THE INVENTION

This invention relates to a process for preparing a 2-amino-1,3-alkanediol or a derivative thereof which is widely useful in organic synthesis, an advantageous process for preparing an optically active dihydrosphingosine derivative useful as an intermediate for synthesizing an active ingredient of pharmaceuticals or cosmetics, and intermediates for preparing the optically active dihydrosphingosine derivative.

BACKGROUND OF THE INVENTION

Optically active dihydrosphingosines, which are obtained by removing the amino group protecting group from optically active dihydrosphingosine derivatives represented by formula (IV):

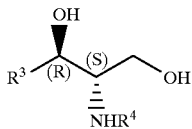

(IV)

wherein $R^3$ represents a straight-chain alkyl group having 7 to 21 carbon atoms; and $R^4$ represents an amino group protecting group (the compound according to the present invention, hereinafter described), are known to be useful as an active ingredient of, for example, dermal preparations for external application (see JP-A-5-85924, the term "JP-A" as used herein means an "unexamined published Japanese patent application"). They are also known as an important constituent of the chemical structures of ceramides having a horny layer moisturizing activity and cerebroside and ganglioside having various biological activities.

Optically active dihydrosphingosines have conventionally been produced by the following processes:

(A) A process comprising optical resolution of racemic dihydrosphingosines.

(B) A process starting with optically active naturally-occurring substances.

(C) A process comprising asymmetric synthesis.

Process (A) involves waste because an unnecessary enantiomer is produced in the same amount as a desired optical isomer.

Process (B) includes the method reported by E. J. Reist, et al. in *J. Org. Chem.*, Vol. 35, p. 3521 (1970), in which an optically active amino sugar is used as a starting material and a Wittig reaction is carried out, and the method reported by T. Hino, et al. in *Chem. Lett.*, p. 1407 (1990), in which L-serine is used as a starting material, and a long-chain alkylene is added thereto, followed by reduction. The former method is impractical due to as low a yield as 30% attained in the Wittig reaction and many steps required; and the latter method is industrially unsuitable because the selectivity to a desired erythro form is only 90% and the starting material L-serine is expensive.

As process (C), W. R. Roush, et al. report in *J. Org. Chem.*, Vol. 50, pp. 3752–3757 (1985) a process comprising a Horner-Emmons reaction of palmitic aldehyde to obtain (2E)-octadec-2-en-1-ol, asymmetric epoxidation of the (2E)-octadec-2-en-1-ol using t-butyl hydroperoxide to obtain an optically active epoxide, reacting the epoxide with sodium hydride to obtain an oxazolidinone derivative, and ring opening to obtain an optically active dihydrosphingosine having 18 carbon atoms. This process is disadvantageous in that highly pure (2E)-octadecan-2-en-1-ol should be prepared in order to obtain an epoxy compound having a high optical purity and that a peroxide, such as t-butyl hydroperoxide, which is an explosive reagent difficult to handle, must be used in quantity.

For preparation of racemic dihydrosphingosines, K. Sisido, et al., report in *J. Org. Chem.*, Vol. 29, No. 9, pp. 2783–2784 (1964) a process comprising, for example, reacting methyl trans-2-octadecenoate with perbenzoic acid in chloroform to obtain methyl 2,3-epoxyoctadecanoate having formula (V'):

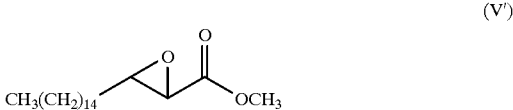

(V')

whose planar structure is the same as that of the compound represented by formula (V) hereinafter described, hydrolyzing the ester (V'), cyclizing the resulting acid by reaction with benzylamine to obtain 2-benzylamino-3-hydroxyoctadecanoic acid (cyclization yield: 68%), converting the acid to a methyl ester, and reducing the ester in an ether solvent with lithium aluminum hydride (LiAlH4) (reduction yield: 71%). Reduction of such a carboxylic acid as 2-benzylamino-3-hydroxyoctadecanoic acid to an alcohol has generally been carried out by once esterifying the carboxylic acid and using $LiAlH_4$ as a reducing agent as in the above report. However, $LiAlH_4$ is a reagent unsuitable to industrial use because it is not only expensive but difficult to handle on account of reactivity with moisture in air.

Use of sodium tetrahydroborate ($NaBH_4$), which is cheaper than $LiAlH_4$, as a reducing agent for reduction of ethyl 2-amino-3-hydroxy-4-octadecanoate structurally similar to the compound of formula (III) according to the invention (hereinafter described) to an alcohol is also reported in A. S. Cavallo, et al., *J. Org. Chem.*, Vol. 59, No. 11, pp. 3240–3242 (1994). In this case, however, the reaction time is as long as 4 days, and many steps are involved, including esterification of the carboxylic acid prior to reduction as in the case of using $LiAlH_4$, so that there is a fear of reduction in yield.

Reduction of an amino acid (e.g., L-valine or L-methionine) or an amino acid derivative (e.g., a hydroxyproline derivative) to a corresponding amino-alcohol without esterifying the carboxyl group has been proposed in A. Abiko, et al., *Tetrahedron Lett.*, Vol. 33, No. 38, pp. 5517–5518 (1992) and T. F. Braish, et al., *J. Org. Chem.*, Vol. 55, pp. 1684–1687, in which reduction is effected using $NaBH_4$ and a Lewis acid catalyst (e.g., boron trifluoride etherate) while generating borane. However, no report is found concerning reduction of such an alkanoic acid that has a chain structure in which an amino-substituted carbon atom adjoins a hydroxyl-substituted carbon atom (for example, a 2-amino-3-hydroxyalkanoic acid of formula (I) used as a starting compound in the invention) by using $NaBH_4$ without esterification.

Preparation of optically active dihydrosphingosines has thus been attempted in various ways, but none of the proposals made to date is not fully satisfactory in optical purity and suitability to industrial mass production from the standpoint of ease in reagent handling and the number of necessary steps.

SUMMARY OF THE INVENTION

An object of the invention is to provide a process for preparing an optically active dihydrosphingosine derivative which makes it feasible to produce an optically active dihydrosphingosine at high optical purity and through a simple process that is safe and easy to industrialize.

In order to solve the above-mentioned problems, the inventors have studied a process comprising reducing a (2R,3R)-2-amino-3-hydroxyalkanoic acid derivative having 10 to 24 carbon atoms with its amino group protected through a single step into a corresponding alcohol, i.e., an optically active dihydrosphingosine derivative. As a result, they have found that the above carboxylic acid can be led to a corresponding alcohol through one step reduction with sodium tetrahydroborate ($NaBH_4$) in the presence of an acid without involving esterification of the carboxylic acid. It has been ascertained that the reduction with $NaBH_4$ widely applies provided that the compound to be reduced has a 2-amino-3-hydroxyalkanoic acid skeleton. The inventors have also synthesized a (2S,3R)-2,3-epoxyalkanoic acid or an ester thereof, which is novel and advantageous for obtaining the above-mentioned starting compound, (2R,3R)-2-amino-3-hydroxyalkanoic acid derivative. The present invention has been completed based on these findings.

The invention provides a process for preparing a 2-amino-1,3-alkanediol or a derivative thereof represented by formula (II):

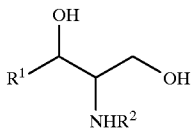

(II)

wherein $R^1$ represents an alkyl group having 1 to 30 carbon atoms; and $R^2$ represents a hydrogen atom or an amino group protecting group, comprising reducing a 2-amino-3-hydroxyalkanoic acid or a derivative thereof represented by formula (I):

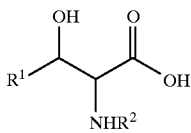

(I)

wherein $R^1$ and $R^2$ are as defined above, with sodium tetrahydroborate ($NaBH_4$) in the presence of an acid (hereinafter referred to as process 1).

The invention provides a process for preparing an optically active dihydrosphingosine derivative represented by formula (IV):

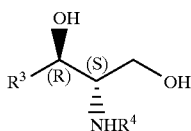

(IV)

wherein $R^3$ represents a straight-chain alkyl group having 7 to 21 carbon atoms; and $R^4$ represents an amino group protecting group, comprising reducing a (2R,3R)-2-amino-3-hydroxyalkanoic acid derivative represented by formula (III):

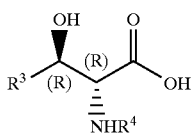

(III)

wherein $R^3$ and $R^4$ are as defined above, with $NaBH_4$ in the presence of an acid (hereinafter referred to as process 2).

The invention provides a process for preparing an optically active dihydrosphingosine derivative represented by formula (IV) comprising reacting a (2S,3R)-2,3-epoxyalkanoic acid or an ester thereof represented by formula (V):

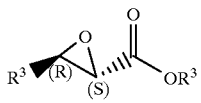

(V)

wherein $R^3$ is as defined above; and $R^5$ represents a hydrogen atom or a lower alkyl group having 1 to 4 carbon atoms, the (2S,3R)-epoxyalkanoic acid ester (V) having been hydrolyzed to a corresponding alkanoic acid (V), with a primary amine represented by formula (VI):

$R^4NH_2$ (VI)

wherein $R^4$ is as defined above, to obtain a (2R,3R)-2-amino-3-hydroxyalkanoic acid derivative represented by formula (III), and reducing the resulting acid derivative with $NaBH_4$ in the presence of an acid (hereinafter referred to as process 3).

The invention also provides novel compounds used as an intermediate in the above processes, i.e., a (2R,3R)-2-amino-3-hydroxyalkanoic acid derivative represented by formula (III) and a (2S,3R)-2,3-epoxyalkanoic acid or its ester represented by formula (V).

DETAILED DESCRIPTION OF THE INVENTION

In process 1 for preparing a 2-amino-1,3-alkanediol or a derivative thereof (II), a 2-amino-3-hydroxyalkanoic acid or a derivative thereof (I) is used as a starting compound.

In formula (I), the alkyl group having 1 to 30 carbon atoms as represented by $R^1$ is not particularly limited and is selected from straight-chain or branched alkyl groups preferably having about 2 to about 25 carbon atoms. The amino group protecting group as represented by $R^2$ in formula (I) is not particularly limited and is selected from those commonly used in organic synthesis. Suitable examples of the protecting group are a benzyl group and a substituted benzyl group, such as a benzyl group, a p-methoxybenzyl group, and a 3,4-methylenedioxybenzyl group.

The formula (I) embraces various steric isomers ascribed to the absolute configuration at the 2-positioned asymmetric carbon atom and/or the 3-positioned asymmetric carbon atom, such as enantiomers (optically active isomers) and racemic modifications thereof, and diastereomers (an erythro form and a threo form). Any of these isomers can be used in process 1. Since the stereoisomerism of the starting compound remains in the reduction product, an appropriate isomer may be chosen according to the end use.

A compound of formula (I) in which $R^1$ is a straight-chain alkyl group having 7 to 21 carbon atoms, $R^2$ is an amino group protecting group, and the 2- and 3-positions have a (2R,3R) configuration corresponds to the (2R,3R)-2-amino-3-hydroxyalkanoic acid derivative (III), which is the starting compound used in process 2. Therefore, use of the compound (III) taken for choice in process 1 leads to preparation of the optically active dihydrosphingosine derivative (IV) as aimed at in process 2.

Examples of the straight-chain alkyl group having 7 to 21 carbon atoms as represented by $R^3$ in formula (III) include n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, and n-heneicosyl groups. Of the compounds (III), those having an n-tridecyl, n-pentadecyl or n-heptadecyl group as $R^3$ provide dihydrosphingosine derivatives (IV) which are used most widely as an intermediate for an active ingredient of pharmaceuticals or cosmetics.

The amino group protecting group as represented by $R^4$ in formula (III) has the same meaning as the protecting group represented by $R^2$ in formula (I). That is, the amino group protecting group $R^4$ is not particularly limited and is selected from those commonly used in organic synthesis, preferably a substituted or unsubstituted benzyl group, such as a benzyl group, a p-methoxybenzyl group, and a 3,4-methylenedioxybenzyl group.

The reduction reaction according to the invention and synthesis of the starting compounds therefor will be explained by referring to process 2. The explanation applies to process 1 as well.

The starting compound, (2R,3R)-2-amino-3-hydroxyalkanoic acid derivative (III), can be obtained by, for example, reacting a (2S,3R)-2,3-epoxyalkanoic acid (V) or an ester thereof (V) having been hydrolyzed to an alkanoic acid with a primary amine (VI) to open the epoxide and preferentially aminating the 2-position according to process 3.

While a racemic 2-amino-3-hydroxyalkanoic acid derivative, the planar structure of which is the same as that of the (2R,3R)-2-amino-3-hydroxyalkanoic acid derivative (III), is a known compound, the optically active 2-amino-3-hydroxyalkanoic acid (III) having a specific steric configuration (2R,3R) is a novel compound that has been synthesized by the inventors for the first time.

In formula (V), the lower alkyl group having 1 to 4 carbon atoms as represented by $R^5$ denotes a straight-chain or branched alkyl group having 1 to 4 carbon atoms, such as methyl, ethyl, n-propyl, isopropyl, n-butyl, and t-butyl groups. A methyl group is preferred of them.

A racemic 2,3-epoxyalkanoic acid or an ester thereof, the planar structure of which is the same as that of the (2S,3R)-2,3-epoxyalkanoic acid or an ester thereof (V), is a known compound. While an optically active compound having the formula (V) but with the straight-chain alkyl group having 7 to 21 carbon atoms as $R^3$ being displaced with a methyl group and having the same steric configuration as the compound (V) is also known (see E. J. Corey, et al., *Tetrahedron Lett.*, Vol. 33, No. 45, pp. 6735–6738 (1992)), the (2S,3R)-2,3-epoxyalkanoic acid or an ester thereof (V) having a considerably longer carbon chain than a methyl group is a novel compound that has been synthesized by the inventors for the first time.

Besides being useful as a starting compound for preparing the optically active dihydrosphingosine derivative (IV) according to process 3, the compound (V) can be reduced at the ester moiety thereof with a reducing agent in a conventional manner to give a (2R,3R)-2,3-epoxyalkanol. This alcohol compound is also a useful compound that can be led to an optically active dihydrosphingosine derivative by ring opening according to the process disclosed, e.g., in J. M. Chong, et al., *J. Org. Chem.*, Vol. 50, pp. 1560–1563 (1985).

Reduction of the ester moiety of the compound (V) can be achieved at high yield by, for example, refluxing in tetrahydrofuran together with $NaBH_4$ as a reducing agent (see Reference Example 1).

The (2S,3R)-2,3-epoxyalkanoic acid or an ester thereof (V) can easily be obtained by, for example, applying the process for preparing a (2S,3R)-2,3-epoxy-4-cyclohexylbutyric acid ester described in JP-A-5-1000. The process is illustrated by the following reaction scheme:

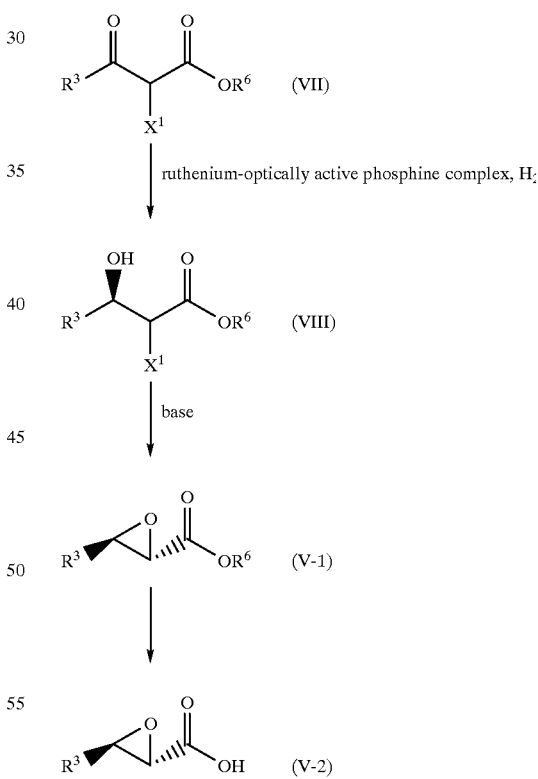

wherein $R^3$ is as defined above; $R^6$ represents a lower alkyl group; and $X^1$ represents a halogen atom.

According to the scheme, a 2-halo-3-oxoalkanoic acid ester (VII) is asymmetrically hydrogenated in the presence of a ruthenium-optically active phosphine complex, and the resulting (3R)-2-halo-3-hydroxyalkanoic acid ester (VIII) is epoxidized with a base to give a (2S,3R)-2,3-epoxyalkanoic acid ester (V-1) (a compound of formula (V) wherein $R^5$ is a lower alkyl group having 1 to 4 carbon atoms). Hydrolysis of the ester (V-1) gives a (2S,3R)-2,3-epoxyalkanoic acid (V-2) (a compound of formula (V) wherein $R^5$ is a hydrogen atom).

The halogen atom as represented by $X^1$ in formula (VII) is preferably a chlorine atom or a bromine atom, with a chlorine atom being preferred. The lower alkyl group as represented by $R^6$ in formula (VII) has the same meaning as the lower alkyl group as $R^5$ in formula (V). That is, $R^6$ is a straight-chain or branched alkyl group having 1 to 4 carbon atoms, including methyl, ethyl, n-propyl, isopropyl, n-butyl, and t-butyl groups. A methyl group is preferred of them.

The 2-halo-3-oxoalkanoic acid ester (VII) is obtained by halogenating a 3-oxoalkanoic acid ester in a known manner. The halogenation is carried out by, for example, dissolving a 3-oxoalkanoic acid ester in an organic solvent, e.g., toluene or ethyl acetate, and adding thereto an approximately equivalent amount of a halogenating agent, such as halogen molecules, a sulfuryl halide (e.g., sulfuryl chloride) or an N-halogen compound (e.g., N-chlorosuccinimide), at about 0 to 5° C., followed by stirring at room temperature for about 12 to 24 hours, preferably overnight, as disclosed in JP-A-63-101387.

The starting 3-oxoalkanoic acid ester (VII) may be a commercially available compound, or it can be synthesized by a known process comprising, for example, reacting an acetoacetic ester with about 1 to 1.1 mols, per mole of the acetoacetic ester, of an acyl chloride having a prescribed carbon chain in an appropriate solvent, e.g., tetrahydrofuran, followed by deacylation.

The ruthenium-optically active phosphine complex used as a catalyst for asymmetric hydrogenation of the 2-halo-3-oxoalkanoic acid ester (VII) preferably includes those represented by formula (IX) or (X):

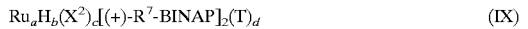
(IX)

wherein $R^7$-BINAP represents a tertiary phosphine ligand having formula (XI):

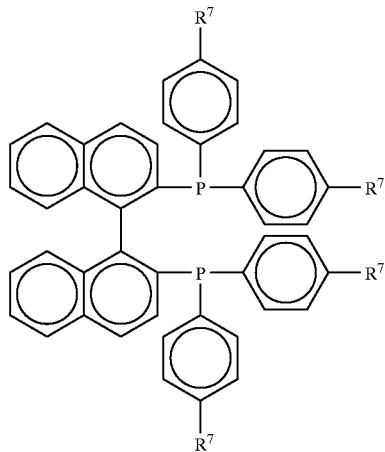
(XI)

$R^7$ represents a hydrogen atom, a methyl group, a t-butyl group or a methoxy group; $X^2$ represents a halogen atom; T represents a tertiary amine; b represents 0 or 1; when b is 0, a, c, and d represent 2, 4 and 1, respectively; when b is 1, a, c, and d represent 1, 1 and 0, respectively.

(X)

wherein $R^7$-BINAP is as defined above; $X^3$ represents a halogen atom; Q represents a substituted or unsubstituted benzene ring; $X^4$ represents the same halogen atom as for $X^3$, or $ClO_4$, $PF_6$, $BF_4$ or $BPh_4$ (Ph represents a phenyl group).

Specific examples of the tertiary phosphine $R^7$-BINAP in formulae (IX) and (X) are:
Phosphine 1: 2,2'-bis(diphenylphosphino)-1,1'-binaphthyl (hereinafter referred to as BINAP)
Phosphine 2: 2,2'-bis(di-p-tolylphosphino)-1,1'-binaphthyl (hereinafter referred to as Tol-BINAP)
Phosphine 3: 2,2'-bis(di-p-t-butylphenylphosphino)-1,1'-binaphthyl (hereinafter referred to as t-Bu-BINAP)
Phosphine 4: 2,2'-bis(di-p-methoxyphenylphosphino)-1,1'-binaphthyl (hereinafter referred to as methoxy-BINAP).

While these tertiary phosphine compounds each include a (+)-compound, a (−)-compound, and a racemic modification thereof, the (+)-compound is to be used in order to obtain a (3R)-2-halo-3-hydroxyalkanoic acid ester (VIII) having a specific steric configuration as a starting compound of process 2. Use of the (−)-compound or a racemic modification gives a (3S)-2-halo-3-hydroxyalkanoic acid ester (VIII) or a racemic 2-halo-3-hydroxyalkanoic acid ester (VIII), respectively, from which a starting compound for preparing the 2-amino-1,3-alkanediol or a derivative thereof used in process 1 can be derived.

These tertiary phosphine compounds can be prepared in accordance with the process described in JP-A-61-63690 or JP-1-68386.

The ruthenium-optically active phosphine complex represented by formula (IX) is prepared by a known process described, e.g., in JP-A-61-63690 and JP-A-1-68386 supra. That is, ruthenium chloride and cycloocta-1,5-diene (hereinafter referred to as COD) are reacted in ethanol to obtain $[Ru(X^2)_2(COD)]_n$ (n is a natural number), which is then reacted with (+)-$R^7$-BINAP by heating in a solvent (e.g., toluene or ethanol) in the presence of a tertiary amine (represented by T). The tertiary amine represented by T includes triethylamine, tributylamine, ethyldiisopropylamine, 1,8-bis(dimethylamino)naphthalene, dimethylaniline, pyridine, and N-methylpiperidine, with triethylamine being preferred. The halogen atom as represented by $X^2$ is preferably a chlorine atom.

Specific examples of the complex (IX) are as follows
Complex 1: $Ru_2Cl_4[(+)\text{-BINAP}]_2NEt_3$ (wherein Et is an ethyl group; hereinafter the same)
Complex 2: $RU_2Cl_4[(+)\text{-Tol-BINAP}]_2NEt_3$
Complex 3: $RU_2Cl_4[(+)\text{-t-Bu-BINAP}]_2NEt_3$
Complex 4: $Ru_2Cl_4[(+)\text{-Methoxy-BINAP}]_2NEt_3$
Complex 5: $RuHCl[(+)\text{-BINAP}]_2$
Complex 6: $RuHCl[(+)\text{-Tol-BINAP}]_2$
Complex 7: $RuHCl[(+)\text{-t-Bu-BINAP}]_2$
Complex 8: $RuHCl[(+)\text{-Methoxy-BINAP}]2$ The ruthenium-optically active phosphine complex represented by formula (X) can be obtained by the process described, e.g., in JP-A-2-191289. That is, the complex (X) where $X^4$ is the same halogen atom as $X^3$ is prepared by reacting $[RuX^3{}_2(Q)]_2$ (wherein $X^3$ and Q are as defined above) with (+)-$R^7$-BINAP in an appropriate solvent. The complex (X) where $X^4$ is $ClO_4$, $PF_6$, $BF_4$ or $BPh_4$ is prepared by reacting the resulting $\{RuX^3(Q)[(+)\text{-}R^7\text{-BINAP}]\}X^3$ with a salt represented by formula: $MX^{4'}$ wherein M represents Na, K, Li, Mg or Ag; and $X^{4'}$ represents $ClO_4$, $PF_6$, $BF_4$ or $BPh_4$.

The substituted or unsubstituted benzene as represented by Q is benzene or benzene substituted with a lower alkyl group, a lower alkoxy group, a lower alkoxycarbonyl group, a halogen atom, etc. The term "lower" as used herein means a straight chain or branched chain having 1 to 4 carbon atoms. Examples of Q are benzene, toluene, xylene, trimethylbenzene, hexamethylbenzene, ethylbenzene, t-butylbenzene, p-cymene, cumene, anisole, methylanisole, methyl benzoate, methyl methylbenzoate, methyl chlorobenzoate, chlorobenzene, dichlorobenzene, trichlorobenzene, bromobenzene, and fluorobenzene. The halogen atom as $X^3$ and $X^4$ is a chlorine atom, a bromine atom or an iodine atom.

Specific examples of the complex (X) are
Complex 9: {RuCl(benzene)[(+)-BINAP]}Cl
Complex 10: {RuCl(benzene)[(+)-Tol-BINAP]}Cl
Complex 11: {RuBr(benzene)[(+)-BINAP]}Br
Complex 12: {RuI(p-cymene)[(+)-BINAP]}I
Complex 13: {RuCl(methyl benzoate)[(+)-BINAP]}Cl
Complex 14: {RuCl(benzene)[(+)-BINAP]}ClO$_4$
Complex 15: {RuCl(benzene)[(+)-t-Bu-BINAP]}ClO$_4$
Complex 16: {RuCl(benzene)[(+)-BINAP]}PF$_6$
Complex 17: {RuCl(benzene)[(+)-BINAP]}BF$_4$
Complex 18: {RuCl(benzene)[(+)-BINAP]}BPh$_4$ The asymmetric hydrogenation of the 2-halo-3-oxoalkanoic acid ester (VII) is carried out by putting in a pressure container having been purged with nitrogen the compound (VII), the ruthenium-optically active phosphine complex, and a solvent and allowing the mixture to react in a hydrogen atmosphere. The ruthenium-optically active phosphine complex as a catalyst is used in an amount of about 0.0001 to 0.01 mol, preferably about 0.0002 to 0.005 mol, per mole of the compound (VII). If it is used in a lesser amount, sufficient catalysis cannot be exerted. Use of a higher amount of the catalyst is uneconomical.

The solvent used is not limited and selected from those used in general asymmetric hydrogenation. Suitable solvents include organic solvents, such as alcohols, e.g., methanol, ethanol, propanol, isopropyl alcohol, butanol, and t-butanol; tetrahydrofuran, methylene chloride, and acetone. While not limiting, the solvent is preferably used in an amount about 2 to 10 times the volume of the compound (VII).

The reaction is carried out at a temperature of about 0 to 80° C., preferably about 30 to 50° C., under a hydrogen pressure of about 10 to 100 atm, preferably about 30 to 50 atm, for a period of about 15 to 30 hours. After completion of the reaction, the solvent is removed by evaporation, and the residue can be used in the next reaction either as obtained or after being purified in a usual manner, such as silica gel column chromatography or recrystallization.

There is thus obtained the (3R)-2-halo-hydroxyalkanoic acid ester (VIII) at a high optical purity. While a racemic 2-halo-3-hydroxyalkanoic acid ester the planar structure of which is the same as that of the (3R)-2-halo-3-hydroxyalkanoic acid ester (VIII) is a known compound, the optically active compound (VIII) having the specific steric configuration is a novel compound.

The base used for epoxidation of the (3R)-2-halo-3-hydroxyalkanoic acid ester (VIII) for obtaining the (2S,3R)-2,3-epoxyalkanoic acid ester (V-1) includes alkali metal alkoxides, such as sodium methoxide, sodium ethoxide, sodium propoxide, sodium isopropoxide, sodium butoxide, sodium t-butoxide, potassium methoxide, potassium ethoxide, potassium propoxide, potassium isopropoxide, potassium butoxide, and potassium t-butoxide; and alkali metal salts, such as sodium carbonate, potassium carbonate, and sodium hydrogencarbonate. Sodium methoxide is preferred of them. The base is used in an amount of about 1 to 2 mol, preferably about 1.01 to 1.10 mol, per moles of the compound (VIII).

The solvent used in the epoxidation includes methanol, ethanol, tetrahydrofuran, and acetone. While not limiting, the solvent is preferably used in an amount about 5 to 20 times the volume of the compound (VIII). The reaction is carried out by adding a solution of the base to a solution of the compound (VIII) at about −20° to 35° C., preferably about 0 to 20° C., and then allowing the mixture to react at room temperature for about 1 to 2 hours.

The reaction mixture is worked up by, for example, removing the solvent by evaporation, adjusting the residue to a pH of about 8 to 9 with a phosphate buffer, etc., extracting the residue with ethyl acetate, isopropyl ether, methylene chloride, chloroform, etc., and removing the extracting solvent by evaporation. If desired, the product may further be purified in a usual manner, for example, by silica gel column chromatography or recrystallization.

In order for the resulting (2S,3R)-2,3-epoxyalkanoic acid ester (V-1) to be opened at the epoxy ring and be aminated, it is necessary to hydrolyze the (2S,3R)-2,3-epoxyalkanoic acid ester (V-1) to the corresponding (2S,3R)-2,3-epoxyalkanoic acid (V-2). The hydrolysis can be conducted in a conventional manner. For example, the compound (V-1) is reacted in a polar solvent, such as methanol or ethanol, in the presence of an adequate amount of a base, such as sodium hydroxide or potassium hydroxide, at room temperature or about 30 to 80° C for about 1 to 20 hours. The reaction mixture is adjusted to a pH of about 5 to 6 with diluted hydrochloric acid, etc., extracted with an organic solvent, such as ethyl acetate, and evaporated to remove the extracting solvent. The product may further be purified in a usual manner, for example, by silica gel column chromatography or recrystallization.

Reaction of the (2S,3R)-2,3-epoxyalkanoic acid (V-2) with a primary amine (VI) gives the (2R,3R)-2-amino-3-hydroxyalkanoic acid derivative (III), which is the starting compound for preparing the optically active dihydrosphingosine derivative according to process 2.

A choice of the primary amine (VI) to be used is made according to the kind of the amino group protecting group $R^4$ in formula (III). Benzylamine is particularly recommended. The primary amine (VI) is preferably used in an amount of about 1 to 3 mol per mole of the compound (V-2). It is recommended to use a base in combination with the primary amine (VI). An aqueous solution of sodium hydroxide is preferably used as a base.

In order to accelerate the reaction, a phase transfer catalyst may be added. The phase transfer catalyst to be used here is selected from those useful in the reduction of the (2R,3R)-2-amino-3-hydroxyalkanoic acid derivative (III) hereinafter described. The amount of the phase transfer catalyst if used, though dependent on the kind of the (2S,3R)-2,3-epoxyalkanoic acid (V-2), is usually about 0.00001 to 0.1 mol per mole of the compound (V-2). Where the compound (V-2) is not easily soluble in the reaction solvent, it is recommended to use the phase transfer catalyst in a somewhat increased amount.

The solvents used in the ring-opening of the epoxide include water, tetrahydrofuran, and dimethoxyethane. While not limiting, the solvent is preferably used in an amount about 5 to 10 times the volume of the compound (V-2). The reaction temperature is from about 0 to 100° C. In a preferred mode, the reaction mixture is set at around room temperature when the phase transfer catalyst is added, about 0 to 5° C. when the primary amine (VI) is added, and then elevated to room temperature to 100° C. at which the reaction mixture is stirred or refluxed for about 1 to 16 hours. After the reaction, the reaction mixture is adjusted to a pH of about 5 to 6 with diluted hydrochloric acid or diluted sulfuric acid, etc., extracted with an organic solvent, such as ethyl acetate or diisopropyl ether, and dried.

Reduction of the resulting (2R,3R)-2-amino-3-hydroxyalkanoic acid derivative (III) with $NaBH_4$ in the presence of an acid results in formation of a desired optically active dihydrosphingosine derivative (IV).

$NaBH_4$ is preferably used in an amount of about 0.5 to 4 mols, still preferably about 2.5 to 3 mol, per mol of the starting compound (III). If added in an amount less than 0.5 mol, $NaBH_4$ produces no effect as a reducing agent. Amounts more than 4 mols are of no economical value.

In order to generate borane which participates in the reaction, $NaBH_4$ is used in the presence of an acid. The acid to be used includes inorganic acids, such as hydrochloric acid and sulfuric acid, and Lewis acids, such as boron trifluoride ethyl etherate ($BF_3.O(C_2H_5)_2$). Preferred of them are hydrochloric acid and sulfuric acid for their inexpensiveness.

While borane can be generated in the presence of other reagents such as iodine, methyl iodide, dimethyl sulfate, methyl p-toluenesulfonate, and methanesulfonic acid, these reagents are unfavorable, for they are not easy to separate in purification of the reduction product.

The acid is preferably used in an amount of about 1 to 2 mols per mole of the starting compound (III). After completion of the reaction, a base, such as a sodium hydroxide aqueous solution, is added to the reaction mixture to neutralize the acid used. The base is added in an amount necessary to neutralize the acid, i.e., an approximately equivalent amount to the acid added.

Any solvent can be used in the reaction of process 2 as far as it is inert to the reaction. Suitable solvents include organic solvents, such as ethers, e.g., tetrahydrofuran, diethyl ether, diisopropyl ether, and dimethoxyethane; and alcohols, e.g., methanol and ethanol. The kind of the solvent to be used is selected appropriately according to the kind of the starting compound (III).

Where the starting compound (III) is hard to dissolve in the above-mentioned organic solvent so that the reduction reaction does not proceed smoothly due to the non-uniformity of the reaction mixture, it is desirable to add a phase transfer catalyst to the reaction system.

The phase transfer catalyst preferably includes compounds represented by formula (XII):

$$R^8R^9R^{10}R^{11}A^+Z^- \quad (XII)$$

wherein $R^8$, $R^9$, $R^{10}$, and $R^{11}$, which may be the same or different, each represent an alkyl, aralkyl or aryl group having 1 to 20 carbon atoms; A+represents an ammonium ion or a phosphonium ion; and $Z^-$ represents a fluoride ion, a chloride ion, a bromide ion, an iodide ion, a hydroxide ion, or a perchlorate ion.

In formula (XII), the alkyl group as represented by $R^8$, $R^9$, $R^{10}$ and $R^{11}$ is a straight-chain or branched alkyl group having 1 to 20 carbon atoms, and the aralkyl group as represented by $R^8$, $R^9$, $R^{10}$ and $R^{11}$ is a straight-chain or branched alkyl group the hydrogen atom of which being substituted with an aryl group. While the number and the kind of the substituent aryl group are not particularly limited as far as the total carbon atom number of the aralkyl group is within a range of from 7 to 20, a phenyl group or a phenyl group having such a substituent as an alkyl group is preferred. The aryl group as represented by $R^8$, $R^9$, $R^{10}$ and $R^{11}$ is one having 6 to 20 carbon atoms and preferably includes a phenyl group and a phenyl group having such a substituent as an alkyl group.

Specific examples of the phase transfer catalyst (XII) are tetramethylammonium fluoride, tetra-n-butylammonium fluoride, tetraethylammonium chloride, tetra-n-propylammonium chloride, tetra-n-butylammonium chloride, methyltri-n-octylammonium chloride, methyltri-n-decylammonium chloride, lauryltrimethylammonium chloride, benzyltriethylammonium chloride, benzyltri-n-propylammonium chloride, benzyltri-n-butylammonium chloride, phenyltrimethylammonium chloride, tetramethylammonium bromide, tetraethylammonium bromide, tetra-n-propylammonium bromide, tetra-n-butylammonium bromide, tetra-n-pentylammonium bromide, tetra-n-hexylammonium bromide, tetra-n-heptylammonium bromide, tetra-n-octylammonium bromide, lauryltrimethylammonium bromide, myristyltrimethylammonium bromide, cetyltrimethylammonium bromide, cetyldimethylethylammonium bromide, benzyltrimethylammonium bromide, tetraethylammonium iodide, tetra-n-butylammonium iodide, ethyltrimethylammonium iodide, methyltri-n-butylammonium iodide, benzyltrimethylammonium iodide, phenyltrimethylammonium iodide, tetra-n-butylammonium hydroxide, cetyltrimethylammonium hydroxide, benzyltriethylammonium hydroxide, phenyltrimethylammonium hydroxide, tetra-n-propylammonium perchlorate, tetra-n-butylammonium perchlorate, benzyltriphenylphosphonium chloride, tetraphenylphosphonium chloride, tetra-n-butylphosphonium bromide, ethyltriphenylphosphonium bromide, n-butyltriphenylphosphonium bromide, n-heptyltriphenylphosphonium bromide, cetyltriphenylphosphonium bromide, tetraphenylphosphonium bromide, methyltriphenylphosphonium iodide, and tetraphenylphosphonium iodide.

The phase transfer catalyst is used in an amount preferably of about 0.00001 to 0.1 mol, still preferably of about 0.00005 to 0.05 mol, per mole of the starting compound (III). If added in an amount less than 0.00001 mol, catalytic action is not exerted. Amounts more than 0.1 mol are of no economical value.

The reduction reaction of process 2 is carried out by uniformly suspending the starting compound (III), $NaBH_4$, an acid, and a phase transfer catalyst if used in a solvent and stirring the suspension usually at about 0 to 30° C. or room temperature. The time required for completion of the reaction is usually about 8 to 30 hours, while somewhat depending on the kind of the starting compound (III), the reaction temperature, and the other conditions.

After completion of the reaction, if necessary, methanol is added to the reaction mixture to decompose excess borane, and a base is added followed by heating with stirring or refluxing to neutralize the acid. The reaction mixture is then worked up in a conventional manner by, for example, separation and extraction, purification by means of column chromatography or crystallization, to obtain a desired optically active dihydrosphingosine derivative (IV).

Removal of the amino protecting group $R^4$ from the resulting optically active dihydrosphingosine derivative (IV) affords an optically active dihydrosphingosine useful as an active ingredient of pharmaceuticals or cosmetics or an intermediate therefore. Removal of the amino protecting group is carried out in a conventional method. For example, a benzyl group as a protecting group can be removed by hydrogenating the optically active dihydrosphingosine derivative (IV) in an alcohol solvent in the presence of a palladium-on-carbon catalyst (see Reference Example 2 hereinafter described).

The thus prepared dihydrosphingosine can further be led to a ceramide derivative useful as an active ingredient of pharmaceuticals or cosmetics or an intermediate therefor (see Reference Example 3 hereinafter described).

According to the present invention, optically active dihydrosphingosine derivatives useful as an intermediate for an active ingredient of pharmaceuticals or cosmetics can be prepared advantageously.

The invention will now be illustrated in greater detail with reference to Examples and Reference Examples, but it should be understood that the invention is not construed as being limited thereto. Unless otherwise indicated, all the percents are by weight.

Equipment and instruments used for measurement of physical properties of the products prepared and the conditions of measurement are as follows.

Melting Point: MP-S3, manufactured by Yanagimoto Syoji K.K.

Optical Rotation: DIP-4, manufactured by Nihon Bunko Kogyo K.K.

$^1$H-NMR: AM-400 (400 MHz), manufactured by Bruker Inc. Internal standard: tetramethylsilane Mass Spectrum (MS): M-80B (ionization potential: 20 eV), manufactured by Hitachi, Ltd.

Elementary Analysis: CHN-2400, manufactured by Perkin Elmer

Gas Chromatography (GC): HP-5890, manufactured by Hewlett Packard; Column: OV-101 Silica Capillary (0.25 mm×25 m), manufactured by G.L. Science Temp.: raised from 100° C. up to 250° C. at a rate of 10° C./min (sample infusion temperature: 200° C.)

High Performance Liquid Chromatography (HPLC): Waters 510, manufactured by Waters Detector: UV Detector Waters 484, manufactured by Waters

EXAMPLE 1

Preparation of Dihydrosphingosine Derivative (IV) [(2S,3R)-2-Benzylamino-1,3-decanediol]

1) Synthesis of Methyl 2-Chloro-3-oxodecanoate (VII)

A dry tetrahydrofuran suspension (4 l) containing 440 g (11 mol) of 60% sodium hydride was cooled to 0° C., and 1.8 l of a tetrahydrofuran solution of 1.161 kg (10 mol) of methyl acetoacetate was added thereto dropwise, followed by stirring at room temperature for 1 hour. To the reaction mixture was added dropwise 1.789 kg (11 mol) of octanoyl chloride at 0 to 5° C., followed by stirring at room temperature overnight. After confirming disappearance of the octanoyl chloride by thin layer chromatography (TLC), tetrahydrofuran was evaporated, and the residue was poured into ice-water and extracted with 8 l of ethyl acetate. Ethyl acetate was evaporated, and the residue was poured into a mixture of 400 g of a 28% methanol solution of sodium methoxide and 1.2 e of methanol and heated at 60 to 65° C. for 6 hours while stirring to conduct deacylation. The product was cooled with ice, adjusted to pH 5 with a 10% sulfuric acid aqueous solution, and extracted with ethyl acetate. The ethyl acetate layer was washed successively with a 5% sodium carbonate aqueous solution and a saturated sodium chloride aqueous solution. The ethyl acetate was evaporated, and the concentrated residue was distilled under reduced pressure to give 1.10 kg (5.5 mol; yield: 50%) of methyl 3-oxodecanoate (boiling point: 121° C./5 mmHg).

In 500 ml of toluene was dissolved 160 g (0.8 mol) of the resulting methyl 3-oxodecanoate, the solution was cooled to 0 to 5° C., and 108 g (0.8 mol) of sulfuryl chloride was added thereto dropwise, followed by stirring at room temperature overnight. Toluene was removed by evaporation to give 187.8 g (0.8 mol; yield: 100% from methyl 3-oxodecanoate) of the title compound.

2) Synthesis of Methyl (3R)-2-Chloro-3-hydroxydecanoate (VIII)

In a 500 ml Hastelloy-made autoclave having been purged with nitrogen were put 100 g (0.426 mol) of the methyl 2-chloro-3-oxodecanoate (VII) prepared in (1) above, 5 ml of a methylene chloride solution of 780 mg (0.426 mmol) of a ruthenium-optically active phosphine complex $Ru_2Cl_4$ [(+)-Tol-BINAP]$_2$NEt$_3$, and 300 ml of methanol, and the mixture was allowed to react at 50° C. under a hydrogen pressure of 30 atm for 18 hours. Methanol was removed by evaporation to yield 95.78 g (0.405 mol; yield: 95.0%) of the title compound.

As a result of HPLC analysis on the ester of the product at the 3-hydroxyl group thereof (obtained by reaction with (R)-(+)-α-methoxy-a-trifluoromethylphenylacetyl chloride), the product was found to be a mixture of (2R, 3R)-compound having an optical purity of 92% e.e. and (2S,3R)-compound having an optical purity of 91% e.e.

$^1$H-NMR (CDCl$_3$, 67 ppm): 0.88 (t, 3H, J=7.0 Hz), 1.25–1.70 (m, 13H), 3.81 (s×2, 3H), 4.05 (m, 1H), 4.19 (d, 0.56H, J=6.7 Hz), 4.32 (d, 0.44H, J=4.0 Hz)

MS: 237 (M$^+$)

Elementary analysis for $C_{11}H_{21}ClO_3$: Calcd. (%): C 55.80; H 8.94 Found (%): C 55.52; H 8.76

3) Synthesis of Methyl (2S,3R)-2,3-Epoxydecanoate (V-1)

To 500 ml of a methanol solution of 90 g (0.384 mol) of the methyl (3R)-2-chloro-3-hydroxydecanoate (VIII) obtained in (2) above was added dropwise 78 g (0.4 mol) of a 28% methanol solution of sodium methoxide at 0 to 5° C., followed by stirring at room temperature for 1 hour. After confirming disappearance of the methyl (3R)-2-chloro-3-hydroxydecanoate (VIII) by TLC, methanol was evaporated. The concentrate was cooled, adjusted to pH 8 to 9 with 500 ml of a phosphate buffer (prepared by dissolving 5.55 g of sodium dihydrogen phosphate (NaH$_2$PO$_4$.2H$_2$O) and 21.5 g of sodium hydrogenphosphate (Na$_2$HPO$_4$.12H$_2$O) in 1 l of water), and extracted with 1 of isopropyl ether. The isopropyl ether was evaporated, and the residue was distilled to obtain 65.3 g (0.326 mol; yield: 85.0%) of the title compound (V-1) (boiling point: 135° C./0.3 mmHg).

GC and $^1$H-NMR analyses on the product revealed that the proportion of a (2S,3R)-compound was 98%.

The product was led to the corresponding alcohol, (2R, 3R)-2,3-epoxydecanol, which was then esterified by reaction with MTPA chloride. HPLC of the ester revealed that the optical purity of the (2S,3R)-compound was 92% e.e. Optical rotation $[\alpha]_D^{25}$=+25.6° (c=1.0, CHCl$_3$)

$^1$H-NMR (CDCl$_3$, δ ppm): 0.88 (t, 3H, J=6.9 Hz), 1.25 (brs, 8H), 1.47 (m, 2H), 1.60 (m, 2H), 3.16 (dt, 1H, J=1.9 Hz, 4.9 Hz), 3.23 (d, 1H, J=1.9 Hz), 3.78 (s, 3H)

MS: 200 (M$^+$)

Elementary analysis for $C_{11}H_{20}O_3$: Calcd. (%): C 65.97; H 10.06 Found (%): C 65.49; H 9.98

4) Synthesis of (2S,3R)-2,3-Epoxydecanoic Acid (V-2)

In 500 ml of methanol were dissolved 60.0 g (0.3 mol) of the methyl (2S,3R)-2,3-epoxydecanoate (V-1) obtained in (3) above and 12.4 g (0.31 mol) of sodium hydroxide, and the solution was stirred at room temperature for 16 hours. After confirming disappearance of the compound (V-1) by TLC, methanol was evaporated, and the concentrate was adjusted to pH 5 to 6 with 500 ml of diluted hydrochloric acid, extracted with 500 ml of ethyl acetate, and dried. Ethyl acetate was evaporated to obtain crude crystals. Recrystallization from 5-fold volume of heptane gave 41.9 g (0.225 mol; yield: 75%) of the title compound (V-2) (melting point: 36–37° C.).

The product was led to the corresponding alcohol, (2R, 3R)-2,3-epoxydecanol, which was then esterified by reaction with MTPA chloride. HPLC of the ester revealed that the optical purity of the product was 95% e.e. Optical rotation $[\alpha]_D^{25}$=+25.6° (c=1.0, CHCl$_3$)

¹H-NMR (CDCl₃, δ ppm): 0.88 (t, 3H, J=7.0 Hz), 1.25 (brs, 8H), 1.45 (m, 2H), 1.60 (m, 2H), 3.18 (d, 1H), 3.21 (d, 1H)

MS: 186 (M⁺)

Elementary analysis for $C_{10}H_{18}O_3$: Calcd. (%): C 64.49; H 9.74 Found (%): C 64.10; H 9.30

5) Synthesis of (2R,3R)-2-Benzylamino-3-hydroxydecanoic acid (III)

To 18,6 g (0.10 mol) of the (2S,3R)-2,3-epoxydecanoic acid (V-2) obtained in (4) above were added 100 ml of water and 150 mg (0.37 mmol) of a phase transfer catalyst "Aliquat 336" (methyltri-n-octylammonium chloride produced by Henckels; hereinafter the same) at room temperature. The mixture was stirred at 2 to 3° C., and 32.1 g (0.30 mol) of benzylamine (VI) was added thereto dropwise, followed by stirring for about 5 minutes. To the mixture was further added 16 ml (0.08 mol) of a 5N sodium hydroxide aqueous solution, followed by refluxing for 2 hours and then stirring at room temperature for 16 hours. The reaction mixture was cooled to 0 to 5° C., 4 ml (0.02 mol) of a 5N sodium hydroxide aqueous solution was added, and the mixture was washed with two 100 ml portions of diisopropyl ether. The aqueous layer was adjusted to pH 5 to 6 by addition of 2N hydrochloric acid aqueous solution while stirring. The precipitated white crystals were washed with water and dried to give 26.7 g (0.091 mol; yield: 91.0%) of the title compound (III) (melting point: 197–199° C.).

The product was reacted with diazomethane to obtain methyl (2R,3R)-2-benzylamino-3-hydroxydecanoate, which is then reacted MTPA chloride to introduce an MTPA group to the 3-hydroxyl group and the 2-benzylamino group. HPLC analysis of this compound revealed that the optical purity of the above obtained product was 95% e.e. Optical rotation $[\alpha]_D^{25}$=+7.92° (c=0.1, CHCl₃:CH₃OH=1:1 by volume)

¹H-NMR (CDCl₃:CD₃OD=1:1, δ ppm): 0.88 (t, 3H, J=7.0 Hz), 1.25 (brs, 8H), 1.45 (m, 2H), 1.55 (m, 2H), 3.50 (d, 1H, J=3.8 Hz), 3.9–4.3 (m, 3H), 7.3–7.5 (5H, aromatic)

MS: 294 (M⁺+1)

Elementary analysis for $C_{17}H_{27}NO_3$: Calcd. (%): C 69.59; H 9.27; N 4.77 Found (%): C 69.48; H 9.30; N 4.80

6) Synthesis of Dihydrosphingosine Derivative (IV) [(2S,3R)-2-Benzylamino-1,3-decanediol]:

To a tetrahydrofuran suspension of 5.55 g (0.15 mol) of NaBH₄ was added 14.65 g (0.05 mol) of the (2R,3R)-2-benzylamino- 3-hydroxydecanoic acid (III) obtained in (5) above at room temperature. Then, 6.31 g (0.0625 mol) of concentrated sulfuric acid dissolved in a 3-fold volume of diisopropyl ether was added thereto dropwise at 0 to 5° C., and 0.59 g (1.5 mmol) of a phase transfer catalyst Aliquat 336 was added while stirring at that temperature, followed by stirring overnight at 20 to 25° C. Methanol was added to the mixture to decompose excess borane. To the reaction mixture was added 25 ml (0.125 mol) of a 5N sodium hydroxide aqueous solution, and the solvent was evaporated at 80 to 90° C. The concentrate was further stirred at 100° C. for 3 hours and extracted with methylene chloride at room temperature. The extract was washed with water, concentrated, and purified by column chromatography to obtain 11.2 g (0.04 mol; yield: 80%) of the title compound (IV) as an oily substance. Optical rotation $[\alpha]_D^{25}$=−7.1° (c=1.0, CHCl₃)

¹H-NMR (CDCl₃, δ ppm): 0.88 (t, 3H, J=7.0 Hz), 1.25 (brs, 8H), 1.50 (m, 4H), 2.61 (m, 1H), 3.72 (dd, 2H, J=1.5 Hz, 4.2 Hz), 3.77 (1H, m), 3.80 (d, 1H, J=13.2 Hz), 3.87 (d, 1H, J=13.2 Hz), 7.30 (5H, aromatic)

MS: 280 (M⁺+1)

Elementary analysis for $C_{17}H_{29}NO_2$: Calcd. (%): C 73.07; H 10.46; N 5.02 Found (%): C 72.98; H 10.26; N 4.96

EXAMPLE 2

Preparation of (2S,3R)-2-Benzylamino-1,3-pentanediol (II)

1) Synthesis of Methyl 2-Chloro-3-oxopentanoate

A solution of 104 g (0.8 mol) of methyl 3-oxopentanoate (available from Wacker Chemical) in 500 ml of toluene was cooled to 0 to 5° C., and 108 g (0.8 mol) of sulfuryl chloride was added thereto dropwise, followed by stirring at room temperature overnight. Toluene was removed by evaporation to give 131.6 g (0.8 mol; yield: 100%) of the title compound.

2) Synthesis of Methyl (3R)-2-Chloro-3-hydroxypentanoate

In a 100 ml Hastelloy-made autoclave having been purged with nitrogen were put 10 g (0.0607 mol) of the methyl 2-chloro-3-oxopentanoate prepared in (1) above, 0.2 ml of a methylene chloride solution of 26 mg (0.144 mmol) of a ruthenium-optically active phosphine complex Ru₂Cl₄[(+)-Tol-BINAP]₂NEt₃, and 30 ml of methanol, and the mixture was allowed to react at 50° C. under a hydrogen pressure of 30 atm for 18 hours. Methanol was removed by evaporation to give 9.61 g (0.0577 mol; yield: 95.0%) of the title compound. Optical rotation $[\alpha]_D^{25}$=+6.35° (c=0.976, CHCl₃)

¹H-NMR (CDCl₃, δ ppm): 1.03 (t, 3H, J=7.5 Hz), 1.67 (m, 2H), 3.81 (s×2, 3H), 4.0–4.1 (m, 1H), 4.20 (d, 0.56H, J=6.7 Hz), 4.32 (d, 0.44H, J=3.9 Hz)

MS: 166.5 (M⁺)

3) Synthesis of Methyl (2S,3R)-2,3-Epoxypentanoate

To 130 ml of a methanol solution of 25.5 g (0.153 mol) of the methyl (3R)-2-chloro-3-hydroxypentanoate obtained in (2) above was added dropwise 30 g (0.155 mol) of a 28% methanol solution of sodium methoxide at 0 to 5° C., followed by stirring at room temperature for 1 hour. After confirming disappearance of the methyl (3R)-2-chloro-3-hydroxypentanoate by TLC, methanol was evaporated. The concentrate was cooled, adjusted to pH 8 to 9 with 120 ml of a phosphate buffer, and extracted with 300 ml of isopropyl ether. The isopropyl ether was evaporated, and the residue was purified by column chromatography to give 16.5 g (0.126 mol; yield: 82.87%) of the title compound.

As a result of GC and ¹H-NMR analyses, the proportion of a (2S,3R)-compound was found to be 98%. Optical rotation $[\alpha]_D^{25}$=+3.0° (c=0.5, CHCl₃)

¹H-NMR (CDCl₃, δ ppm): 1.03 (t, 3H, J=7.5 Hz), 1.68 (m, 2H), 3.16 (dt, 1H, J=1.9 Hz, 4.9 Hz), 3.24 (d, 1H, J=1.9 Hz), 3.78 (s, 3H)

MS: 130 (M⁺)

4) Synthesis of (2S,3R)-2,3-Epoxypentanoic Acid

In 50 ml of methanol were dissolved 6.24 g (0.02 mol) of the methyl (2S,3R)-2,3-epoxypentanoate obtained in (3) above and 0.74 g (0.02 mol) of sodium hydroxide, and the solution was stirred for 3 hours. After confirming disappearance of methyl (2S,3R)-2,3-epoxypentanoate by TLC, methanol was evaporated. The concentrate was adjusted to pH 5 to 6 with 50 ml of diluted hydrochloric acid and extracted with 50 ml of ethyl acetate. The extract was dried, and ethyl acetate was removed by evaporation. The residue was purified by column chromatography to obtain 4.26 g (0.015 mol; yield: 75%) of the title compound. Optical rotation $[\alpha]_D^{25}$=+6.07° (c=1.07, CHCl₃)

¹H-NMR (CDCl₃, δ ppm): 1.03 (t, 3H, J=7.5 Hz), 1.67 (m, 2H), 3.16 (d, 1H), 3.21 (d, 1H), 7.2 (br, 1H)

MS: 116 (M⁺)

5) Synthesis of (2R,3R)-2-Benzylamino-3-Hydroxypentanoic Acid

To 14.2 g (0.05 mol) of the (2S,3R)-2,3-epoxypentanoic acid obtained in (4) above were added 500 ml of water and 6.4 g (0.16 mol) of sodium hydroxide, and 42.6 g (0.15 mol) of benzylamine (VI) was added thereto, followed by refluxing for 8 hours. Water was evaporated, and the concentrate was adjusted to pH 5 to 6 with diluted hydrochloric acid and extracted with 500 ml of ethyl acetate. After drying, ethyl acetate was removed by evaporation to yield 8.36 g (0.0375 mol, 75%) of the title compound. Optical rotation $[\alpha]_D^{25}$=+12.84° (c=0.1, CHCl$_3$:CH$_3$OH=1:1 by volume)

$^1$H-NMR (CDCl$_3$:CD$_3$OD=1:1, δ ppm): 0.88 (t, 3H, J=7.3 Hz), 1.40–1.60 (m, 2H), 3.50 (d, 1H, J=3.7 Hz), 3.90 (m, 1H), 4.10–4.30 (m, 2H), 7.3–7.5 (5H, aromatic)

MS: 224 (M$^+$+1)

6) Synthesis of (2S,3R)-2-Benzylamino-1,3-pentanediol

In 100 ml of dimethoxyethane was suspended 8.0 g (0.0358 mol) of (2R,3R)-2-benzylamino-3-hydroxypentanoic acid obtained in (5) above, and 3.31 g (0.0895 mol) of NaBH$_4$ were added thereto, followed by stirring at room temperature for 18 hours. To the mixture was added 3.06 g (0.0625 mol) of concentrated sulfuric acid at 0 to 5° C., and the mixture was stirred at 20 to 25° C. overnight. To the reaction mixture was added 25 ml (0.125 mol) of a 5N sodium hydroxide aqueous solution, followed by heat-refluxing for 5 hours. After completion of the reaction, the reaction mixture was extracted with isopropyl ether to give 5.225 g (0.025 mol, yield: 70%) of the title compound. Optical rotation $[\alpha]_D^{25}$=−11.85° (c=0.54, CHCl$_3$)

$^1$H-NMR (CDCl$_3$, δ ppm): 0.88 (t, 3H, J=7.0 Hz), 1.25 (br, 2H), 1.50 (m, 4H), 2.61 (m, 1H), 3.70 (dd, 2H, J=1.5 Hz, 4.2 Hz), 3.77 (m, 1H), 3.80 (d, 1H, J=13.0 Hz), 3.87 (d, 1H, J=13 Hz), 7.20–7.30 (5H, aromatic)

MS: 210 (M$^+$+1)

EXAMPLE 3

Preparation of Dihydrosphingosine Derivative (IV) [(2S,3R)-2-Benzylamino-1,3-octadecanediol)]

1) Synthesis of Methyl 2-Chloro-2-oxooctadecanoate (VII)

A dry tetrahydrofuran suspension (2 l) of 228 g (5.7 mol) of 60% sodium hydride was cooled to 0° C., and 1.8 l of a tetrahydrofuran solution of 638 g (5.5 mol) of methyl acetoacetate was added thereto dropwise, followed by stirring at room temperature for 1 hour. To the mixture was added dropwise 1.511 kg (5.5 mol) of palmitoyl chloride at 0 to 5° C. followed by stirring at room temperature overnight. After confirming disappearance of palmitoyl chloride by TLC, tetrahydrofuran was evaporated, and the residue was poured into ice-water and extracted with 2 l of ethyl acetate. Ethyl acetate was evaporated, and the residue was poured into a mixture of 400 g of a 28% methanol solution of sodium methoxide and 1.2 l of methanol. The mixture was heated at 60 to 65° C. for 6 hours while stirring to conduct deacylation. The product was cooled with ice, adjusted to pH 5 with a 10% sulfuric acid aqueous solution, and extracted with ethyl acetate. The ethyl acetate layer was washed successively with a 5% sodium carbonate aqueous solution and a saturated sodium chloride aqueous solution. Ethyl acetate was removed by evaporation, and the resulting crude crystals were recrystallized from methanol to give 858 g (2.75 mol; yield: 50.0%) of methyl 3-oxooctadecanoate (melting point: 45° C.).

In 500 ml of toluene was dissolved 249.6 g (0.8 mol) of the resulting methyl 3-oxooctadecanoate, and the solution was cooled to 0 to 5° C. To the solution was added dropwise 108 g (0.8 mol) of sulfuryl chloride, followed by stirring at room temperature overnight. Toluene was evaporated to obtain 277.2 g (0.8 mol; yield: 100% from methyl 3-oxooctadecanoate) of the title compound (melting point: 38° C.).

2) Synthesis of Methyl (3R)-2-Chloro-3-hydroxyoctadecanoate (VIII)

In a 500 ml Hastelloy-made autoclave having been purged with nitrogen were put 100 g (0.2886 mol) of the methyl 2-chloro-3-oxooctadecanoate (VII) prepared in (1) above, 2 ml of a methylene chloride solution of 260 mg (0.144 mol) of a ruthenium-optically active phosphine complex Ru$_2$Cl$_4$[($^+$)-Tol-BINAP]$_2$NEt$_3$, and 300 ml of methanol, and the mixture was allowed to react at 50° C. under a hydrogen pressure of 30 atm for 18 hours. Methanol was removed by evaporation to give 95.8 g (0.275 mol; yield: 95.3%) of the title compound (VIII) (melting point: 39–40° C.).

The product was reacted with MTPA chloride in a usual manner to esterify the 3-hydroxyl group thereof. HPLC of the ester revealed that the product was a mixture of a (2R,3R)-compound having an optical purity of 89% e.e. and a (2S,3R)-compound having an optical purity of 91% e.e.

$^1$H-NMR (CDCl$_3$, δ ppm): 0.88 (t, 3H, J=7.0 Hz), 1.25–1.70 (m, 29H), 3.81 (s×2, 3H), 4.00–4.10 (m, 1H), 4.20 (d, 0.56H, J=6.7 Hz), 4.32 (d, 0.44H, J=3.9 Hz)

MS: 349 (M$^+$)

Elementary analysis for C$_{19}$H$_{37}$ClO$_3$: Calcd. (%): C 65.39; H 10.69 Found (%): C 65.21; H 10.55

3) Synthesis of Methyl (2S,3R)-2,3-Epoxyoctadecanoate (V-1)

To 1.3 l of methanol solution of 262 g (0.75 mol) of the methyl (3R)-2-chloro-3-hydroxyoctadecanoate (VIII) obtained in (2) above was added dropwise 150 g (0.777 mol) of a 28% methanol solution of sodium methoxide at 0 to 5° C. The mixture was stirred at room temperature for 1 hour. After confirming disappearance of the compound (VIII) by TLC, methanol was evaporated. The concentrate was cooled, adjusted to pH 8 to 9 with 1.2 l of a phosphate buffer, and extracted with 3 l of isopropyl ether. Isopropyl ether was evaporated, and the resulting crude crystals were recrystallized from heptane to give 165 g (0.529 mol; yield: 70.5%) of the title compound (V-1) (melting point: 54–55° C.).

GC and $^1$H-NMR analyses revealed that the proportion of a (2S,3R)-compound was 98%.

The product was led to the corresponding alcohol, (2R, 3R)-2,3-epoxyoctadecanol (see Reference Example 1), which was then esterified by reaction with MTPA chloride. HPLC of the ester revealed that the optical purity of the product was 95% e.e. Optical rotation $[\alpha]_D^{25}$=+13.5° (c=0.511, CHCl$_3$)

$^1$H-NMR (CDCl$_3$, δ ppm): 0.88 (t, 3H, J=6.9 Hz), 1.25 (brs, 24H), 1.45 (m, 2H), 1.60 (m, 2H), 3.18 (dt, 1H, J=2.0 Hz, 4.9 Hz), 3.21 (d, 1H, J=2.0 Hz), 3.78 (s, 3H)

MS: 312 (M$^+$)

Elementary analysis for C$_{19}$H$_{36}$O$_3$: Calcd. (%): C 73.03; H 11.61 Found (%): C 72.98; H 11.22

4) Synthesis of (2S,3R)-2,3-Epoxyoctadecanoic Acid (V-2)

In 500 ml of methanol were dissolved 62.4 g (0.2 mol) of the methyl (2S,3R)-2,3-epoxyoctadecanoate (V-1) obtained in (3) above and 7.4 g (0.2 mol) of sodium hydroxide, and the solution was stirred for 3 hours. After confirming disappearance of the compound (V-1) by TLC, methanol was evaporated. The resulting concentrate was adjusted to pH 5 to 6 with 500 ml of diluted hydrochloric acid and extracted with 500 ml of ethyl acetate. After drying, ethyl acetate was evaporated, and the resulting crude crystals were recrystallized from a 5-fold volume of heptane to afford 42.6 g (0.15 mol; yield: 75%) of the title compound (V-2) (melting point: 186° C.).

The product was led to the corresponding alcohol, (2R, 3R)-2,3-epoxyoctadecanol, which was then esterified by reaction with MTPA chloride. HPLC of the ester revealed that the optical purity of the product was 95% e.e. Optical rotation $[\alpha]_D^{25}=+6.5°$ (c=0.246, CHCl$_3$)

$^1$H-NMR (CDCl$_3$, δ ppm): 0.88 (t, 3H, J=7.0 Hz), 1.25 (brs, 24H), 1.45 (m, 2H), 1.60 (m, 2H), 3.18 (dt, 1H, J=1.9 Hz, 5.0 Hz), 3.21 (d, 1H, J=1.9 Hz)

MS: 298 (M$^+$)

Elementary analysis for C$_{18}$H$_{34}$O$_3$: Calcd. (%): C 72.44; H 11.48 Found (%): C 72.41; H 11.43

5) Synthesis of (2R,3R)-2-Benzylamino-3-hydroxyoctadecanoic Acid (III)

To 44.7 g (0.15 mol) of the (2S,3R)-2,3-epoxyoctadecanoic acid (V-2) obtained in (4) above were added 150 ml of water and 1.6 g (4 mmol) of a phase transfer catalyst Aliquat 336 at room temperature, followed by stirring at 2 to 3° C. To the mixture was added dropwise 48.2 g (0.45 mol) of benzylamine (VI), followed by further stirring for about 5 minutes. To the mixture was added 24.0 ml (0.12 mol) of a 5N sodium hydroxide aqueous solution, and the mixture was refluxed for 2 hours and then stirred at room temperature for 16 hours. The reaction mixture was cooled to 0 to 5° C., 6.0 ml (0.03 mol) of a 5N sodium hydroxide aqueous solution was added thereto, and the mixture was extracted with 800 ml of diisopropyl ether. The aqueous layer was adjusted to pH 5 to 6 with 2N hydrochloric acid aqueous solution, and the precipitated white crystals were extracted with 1600 ml of diisopropyl ether and collected by filtration under ice-cooling to obtain 55.3 g (0.137 mol; yield: 91.0%) of the title compound (melting point: 132° C.).

The product was reacted with diazomethane to obtain methyl (2R,3R)-2-benzylamino-3-hydroxyoctadecanoate, which was then reacted with MTPA chloride to introduce an MTPA group to the 3-hydroxyl group and the 2-benzylamino group. HPLC analysis of this compound revealed that the optical purity of the above obtained product was 95% e.e. Optical rotation $[\alpha]_D^{25}=+11.0°$ (c=0.1, CHCl$_3$:CH$_3$OH=1:1 by volume)

$^1$H-NMR (CDCl$_3$:CD$_3$OD=1:1, δ ppm): 0.88 (t, 3H, J=7.0 Hz), 1.25 (brs, 24H), 1.45 (m, 2H), 1.55 (m, 2H), 3.50 (d, 1H, J=3.8 Hz), 3.90–4.30 (m, 3H), 7.3–7.5 (5H, aromatic)

MS: 360 (M$^+$–45)

Elementary analysis for C$_{25}$H$_{43}$NO$_3$: Calcd. (%): C 74.03; H 10.68; N 3.45 Found (%): C 73.99; H 10.65; N 3.42

6) Synthesis of Dihydrosphingosine Derivative (IV) [(2S,3R)-2-Benzylamino-1,3-octadecanediol]

In 300 ml of tetrahydrofuran was suspended 36.0 g (0.1 mol) of the (2R,3R)-2-benzylamino-3-hydroxyoctadecanoic acid (III) obtained in (5) above, and 9.45 g (0.25 mol) of NaBH$_4$ and 1.0 g (2.5 mmol) of a phase transfer catalyst Aliquat 336 were added thereto, followed by stirring at room temperature for 18 hours. Then, 12.25 g (0.125 mol) of sulfuric acid was added thereto at 0 to 5° C., and the mixture was stirred at 20 to 25° C. overnight. After completion of the reaction, the reaction mixture was extracted with isopropyl ether to obtain 27.5 g (0.07 mol; yield: 70%) of the title compound (melting point: 69–70° C.) Optical rotation $[\alpha]_D^{25}=-5.27°$ (c=1.0, CHCl$_3$) $^1$H-NMR (CDCl$_3$, δ ppm): 0.88 (t, 3H, J=7.0 Hz), 1.25 (brs, 24H), 1.50 (m, 4H), 2.35 (br, 3H), 2.61 (m, 1H), 3.70 (dd, 2H, J=1.5 Hz, 4.2 Hz), 3.77 (m, 1H), 3.80 (d, 1H, J=13.0 Hz), 3.87 (d, 1H, J=13 Hz), 7.20–7.30 (5H, aromatic)

MS: 392 (M$^+$+1)

Elementary analysis for C$_{25}$H$_{45}$NO$_2$: Calcd. (%): C 76.67; H 11.58; N 3.58 Found (%): C 76.64; H 11.54; N 3.55

REFERENCE EXAMPLE 1

Synthesis of (2R,3R)-2,3-Epoxyoctadecanol by Reduction of Methyl (2S,3R)-2,3-Epoxyoctadecanoate (V-1)

In 500 ml of tetrahydrofuran were suspended 62.4 g (0.2 mol) of the methyl (2S,3R)-2,3-epoxyoctadecanoate (V-1) prepared in Example 3-(3) and 7.4 g (0.2 mol) of NaBH$_4$, followed by heat refluxing for 3 hours. After confirming disappearance of the compound (V-1) by TLC, tetrahydrofuran was evaporated. To the residue were added 20 ml of water and then 500 ml of a saturated ammonium chloride aqueous solution to adjust to pH 5 to 6, and the mixture was extracted with 500 ml of ethyl acetate. After drying, ethyl acetate was removed by evaporation, and the resulting crude crystals were recrystallized from heptane to obtain 42.6 g (0.15 mol; yield: 75%) of (2R,3R)-2,3-epoxyoctadecanol (melting point: 77 to 78° C.). Optical rotation $[\alpha]_D^{25}=+24.5°$ (c=0.285, CHCl$_3$)

$^1$H-NMR (CDCl$_3$, δ ppm): 0.87 (t, 3H, J=6.6 Hz), 1.23–1.57 (m, 27H), 1.65 (dd, 2H, J=5.6 Hz, 7.3 Hz), 2.91 (m, 2H), 3.61 (ddd, 1H, J=3.1 Hz, 4.2 Hz, 12.6 Hz), 3.90 (ddd, 1H, J=2.5 Hz, 5.5 Hz, 12.6 Hz)

MS: 284 (M$^+$)

REFERENCE EXAMPLE 2

Synthesis of Dihydrosphingosine [(2S,3R)-2-Amino-1,3-octadecanediol] by Hydrogenation of (2S,3R)-2-Benzylamino-1,3-octadecanediol (IV)

In 15 ml of ethanol was dissolved 1.2 g (2.6 mmol) of the (2S,3R)-2-benzylamino-1,3-octadecanediol (IV) obtained in Example 3, and 51 mg of 5% palladium-on-carbon was added thereto to carry out hydrogenation under a hydrogen pressure of 10 atm. After the reaction, the catalyst was removed, and ethanol was evaporated to obtain 665 mg (2.21 mmol; yield: 85%) of the title compound (melting point; 86–88° C.). Optical rotation $[\alpha]_D^{25}=+5.8°$ (c=1.0, CHCl$_3$:CH$_3$OH=10:1 by volume)

$^1$H-NMR (D-pyridine, δ ppm): 0.87 (t, 3H, J=7.0 Hz), 1.28–1.40 (m, 24H), 1.55 (m, 1H), 1.80 (m, 3H), 3.25 (m, 1H), 3.97 (m, 1H), 4.07 (dd, 1H, J=7.2 Hz, 10.4 Hz), 4.25 (dd, 1H, J=4.4 Hz, 10.4 Hz)

MS: 302 (M$^+$+1)

REFERENCE EXAMPLE 3

Synthesis of Dihydroceramide [(2S,3R)-N-Myristoyl-dihydrosphingosine] from Dihydrosphingosine In 10 ml of tetrahydrofuran was dissolved 520 mg (1.72 mmol) of the dihydrosphingosine obtained in Reference Example 2, and 610 mg (1.75 mmol) of p-nitrophenyl myristate and 5 mg of dimethylaminopyridine were added thereto, followed by stirring at room temperature for 18 hours. Sodium carbonate was added to the reaction mixture to neutralize the produced p-nitrophenol. The resulting tetrahydrofuran solution was filtered, tetrahydrofuran was evaporated, and the concentrate was extracted with ethyl acetate. The ethyl acetate layer was washed with a 5% sodium carbonate aqueous solution. Ethyl acetate was evaporated, and the resulting crude product was recrystallized from heptane to give 838 mg (1.64 mmol; yield: 95%) of dihydroceramide (melting point: 101–102° C.). Optical rotation $[\alpha]_D^{25}=+3.27°$ (c=0.122, CHCl$_3$)

$^1$H-NMR (CDCl$_3$, δ ppm): 0.88 (t, 3H×2, J=7.0 Hz), 1.27 (brs, 48H), 1.54 (m, 2H), 1.64 (m, 2H), 2.23 (dd, 2H, J=7.4 Hz, 7.8 Hz), 2.30 (br, 3H), 3.76 (dd, 1H, J=3.1Hz, 11.3 Hz), 3.78 (1H, m), 3.84 (m, 1H), 4.00 (dd, 1H, J=3.5 Hz, 11.3 Hz), 6.37 (d, 1H, J=7.8 Hz)

MS: 494(M$^+$–17)

While the invention has been described in detail and with reference to specific examples thereof, it will be apparent to one skilled in the art that various changes and modifications can be made therein without departing from the spirit and scope thereof.

What is claimed is:

1. A process for preparing a 2-amino-1,3-alkanediol or a derivative thereof represented by formula (II):

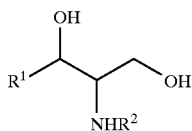

(II)

wherein $R^1$ represents an alkyl group having 1 to 30 carbon atoms; and $R^2$ represents a hydrogen atom or an amino group protecting group, comprising reducing a 2-amino-3-hydroxyalkanoic acid or a derivative thereof represented by formula (I):

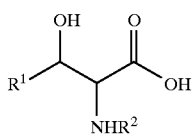

(I)

wherein $R^1$ and $R^2$ are as defined above, with sodium tetrahydroborate in the presence of an acid, wherein said reducing is carried out in the co-presence of a phase transfer catalyst.

2. A process for preparing an optically active dihydrosphingosine derivative represented by formula (IV):

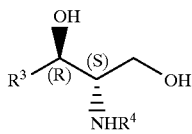

(IV)

wherein $R^3$ represents a straight-chain alkyl group having 7 to 21 carbon atoms; and $R^4$ represents an amino group protecting group, comprising reducing a (2R,3R)-2-amino-3-hydroxyalkanoic acid derivative represented by formula (III):

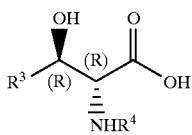

(III)

wherein $R^3$ and $R^4$ are as defined above, with sodium tetrahydroborate in the presence of an acid, wherein said reducing is carried out in the co-presence of a phase transfer catalyst.

3. A process for preparing an optically active dihydrosphingosine derivative represented by formula (IV):

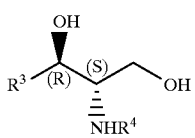

(IV)

wherein $R^3$ represents a straight-chain alkyl group having 7 to 21 carbon atoms; and $R^4$ represents an amino group protecting group, comprising reacting a (2S,3R)-2,3-epoxyalkanoic acid or an ester thereof represented by formula (V):

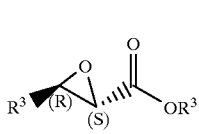

(V)

wherein $R^3$ is as defined above; and $R^5$ represents a hydrogen atom or a lower alkyl group having 1 to 4 carbon atoms, said (2S,3R)-epoxyalkanoic acid ester having been hydrolyzed to a corresponding alkanoic acid, with a primary amine represented by formula (VI):

$R^4NH_2$ (VI)

wherein $R^4$ is as defined above, to obtain a (2R,3R)-2-amino-3-hydroxyalkanoic acid derivative represented by formula (III):

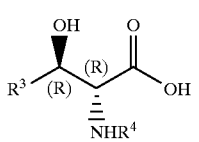

(III)

wherein $R^3$ and $R^4$ are as defined above, and reducing the resulting acid derivative with sodium tetrahydroborate in the presence of an acid, wherein said reducing of the (2R,3R)-2-amino-3-hydroxyalkanoic acid derivative is carried out in the co-presence of a phase transfer catalyst.

* * * * *